United States Patent [19]

Mazza et al.

[11] Patent Number: 4,951,512

[45] Date of Patent: Aug. 28, 1990

[54] SYSTEM FOR PROVIDING ACCESS TO SEALED CONTAINERS

[75] Inventors: John C. Mazza, El Toro; William A. Stark, Costa Mesa, both of Calif.

[73] Assignee: Baxter International Inc., Deerfield, Ill.

[21] Appl. No.: 210,695

[22] Filed: Jun. 23, 1988

[51] Int. Cl.$^5$ .................. G01N 35/04; G01N 35/06
[52] U.S. Cl. ................... 73/861.23; 73/863.85;
73/864.74; 73/866.5; 141/329; 141/130; 422/64; 422/66
[58] Field of Search ............ 73/863.85, 866.5, 864.74, 73/864.23, 864.22, 864.24, 864.25, 864.91, 864.84, 864.85, 864.86, 864.87; 141/329, 330, 130; 422/64, 66; 436/45, 47, 48

[56] References Cited

U.S. PATENT DOCUMENTS

| | | | |
|---|---|---|---|
| 1,930,182 | 10/1933 | Richardson | 152/12 |
| 2,256,656 | 9/1941 | Swabacker | 128/214 |
| 2,503,147 | 4/1950 | Applezweig | 226/116 |
| 2,584,397 | 2/1952 | Pitman | 226/116 |
| 2,689,562 | 9/1954 | Adams et al. | 128/214 |
| 2,855,929 | 10/1958 | Hein, Jr. | 128/221 |
| 3,817,090 | 6/1974 | Michel | 73/81 |
| 3,900,289 | 8/1975 | Liston | 23/230 R |
| 3,991,627 | 11/1976 | Laird et al. | |
| 4,038,874 | 8/1977 | Baldin et al. | 73/864.87 X |
| 4,046,511 | 9/1977 | Stabile | |
| 4,080,833 | 3/1978 | Huber | |
| 4,106,701 | 8/1978 | Siefken | 239/271 |

(List continued on next page.)

FOREIGN PATENT DOCUMENTS 0061317 9/1982 European Pat. Off. .

OTHER PUBLICATIONS

Drawing Showing Rubber Stopper Puncher Mechanism Manufactured by Cavro Scientific Instrument Inc., 242 Humboldt Court, Sunnyvale, Calif. 94089, Dated 9/28/1987.

*How To Use The CleanTech System.* (4 Page Pamphlet from CleanTech Published by Nov. 1988.)
*Factors Influencing the Coring of Rubber Closures,* G. H. Hopkins, Oct. 15, 1958. Technical Report No. 9, 6 Pages, (from The West Company of Phoenixville, PA).
*Coring: The Unseen Menace,* Peter A. Charlebois, B. SC., M. D., Can. Anaes. Soc. J., vol. 13, No. 6, Nov. 1966, pp. 585-597.
*New Developments In Hypodermic Needles,* Brian E. Baldwin, Bulletin of the Parenteral Drug Association, Nov.-Dec., 1971, vol. 25, No. 6, pp. 270-278.
*Purchasing Digest/Needle Sharpness,* N. J. Menolasino, Ph.D. and H. H. Hetz, M. D.; 2 Pages, Published by Nov. 1988.
*The Mechanism of Aging of Elastomers: I. Modes of Degradation and Protective Measures,* George H. Hopkins and Frank M. Keim, Bulletin of the Parenteral Drug Association, Jul.-Aug., 1977, vol. 31, No. 4, pp. 201-210.

Primary Examiner—Tom Noland
Attorney, Agent, or Firm—Marjorie D. Hunter; Michael Bucklo

[57] ABSTRACT

An improved system (10) is provided for providing access to a sealed container (14) which temporarily provides an opening in the closures of the containers, and either removes contents, senses properties of the contents, or dispenses material into the container. In one embodiment, this system includes a carousel assembly (12) which receives sample containers and moves them to a first location. There, a lift assembly (31) moves each sample container upward against a puncture tube (55) of a penetrating assembly (32). This puncture tube provides an opening in the closure of the container. The system takes a sample through this opening or inserts a probe (65) through the opening to measure the properties of the sample. After the system has performed the sampling, sensing, or dispensing function, a stripper assembly (67) strips the container from the puncture tube, allowing the opening to close.

9 Claims, 6 Drawing Sheets

U.S. PATENT DOCUMENTS

| | | | |
|---|---|---|---|
| 4,123,173 | 10/1978 | Bullock et al. | 356/246 |
| 4,131,426 | 12/1978 | Range | 422/100 X |
| 4,143,658 | 3/1979 | Rambosek et al. | 128/184 |
| 4,166,094 | 8/1979 | Froehlich et al. | 422/64 |
| 4,180,071 | 12/1979 | Oiwa | 128/218 N |
| 4,203,443 | 5/1980 | Genese | 128/272.3 |
| 4,210,724 | 7/1980 | Sogi et al. | 435/292 |
| 4,215,690 | 8/1980 | Oreopoulos et al. | 128/221 |
| 4,235,840 | 11/1980 | Mendoza et al. | 422/64 |
| 4,298,570 | 11/1981 | Lillig et al. | 422/64 |
| 4,340,390 | 7/1982 | Collins et al. | 23/230 B |
| 4,343,766 | 8/1982 | Sisti et al. | 422/63 |
| 4,363,781 | 12/1982 | Akamatsu et al. | 422/65 |
| 4,429,584 | 2/1984 | Beyer et al. | 73/864.25 X |
| 4,475,411 | 10/1984 | Wellerfors | 73/864.24 |
| 4,477,190 | 10/1984 | Liston et al. | 356/418 |
| 4,478,095 | 10/1984 | Bradley et al. | 73/864.21 |
| 4,528,159 | 7/1985 | Liston | 422/65 |
| 4,577,514 | 3/1986 | Bradley et al. | 73/863.01 |
| 4,595,562 | 6/1986 | Liston et al. | 422/65 |
| 4,647,432 | 3/1987 | Wakatake | 422/64 |
| 4,656,007 | 4/1987 | Douchy et al. | 422/64 |
| 4,662,231 | 5/1987 | Schaarschmidt et al. | 73/864.23 X |
| 4,665,758 | 5/1987 | Schaarschmidt | 73/864.23 X |
| 4,669,321 | 6/1987 | Meyer | 73/863.85 |
| 4,703,762 | 11/1987 | Rathbone et al. | 128/763 |
| 4,715,413 | 12/1987 | Backlund et al. | 73/864.24 X |
| 4,721,137 | 1/1988 | Muller | 141/65 |
| 4,788,871 | 12/1988 | Nelson et al. | 73/866.5 |
| 4,834,944 | 5/1989 | Wakatake | 422/67 x |
| 4,841,786 | 6/1989 | Schulz | 73/864.25 |

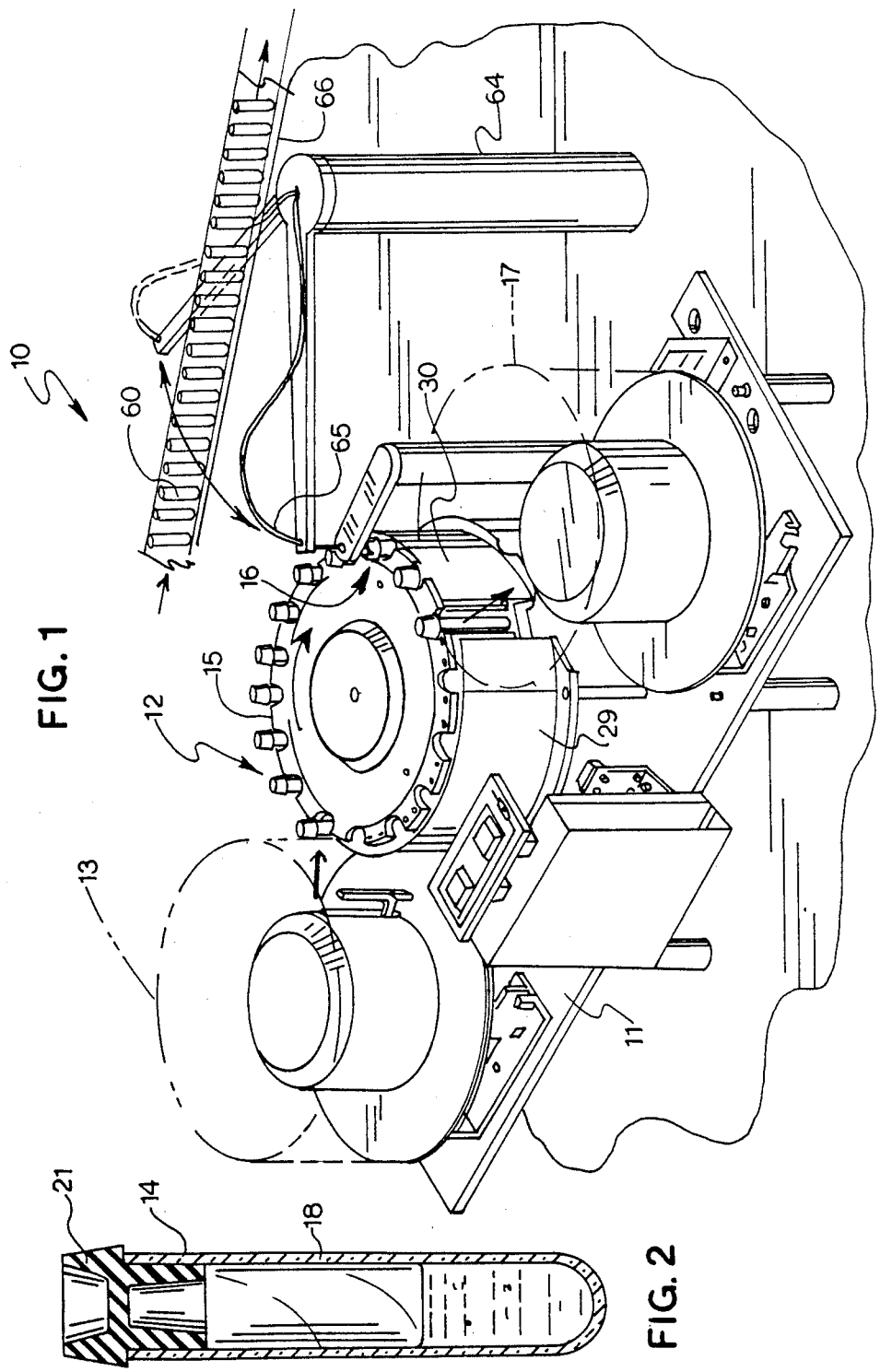

FIG. 6
FIG. 5
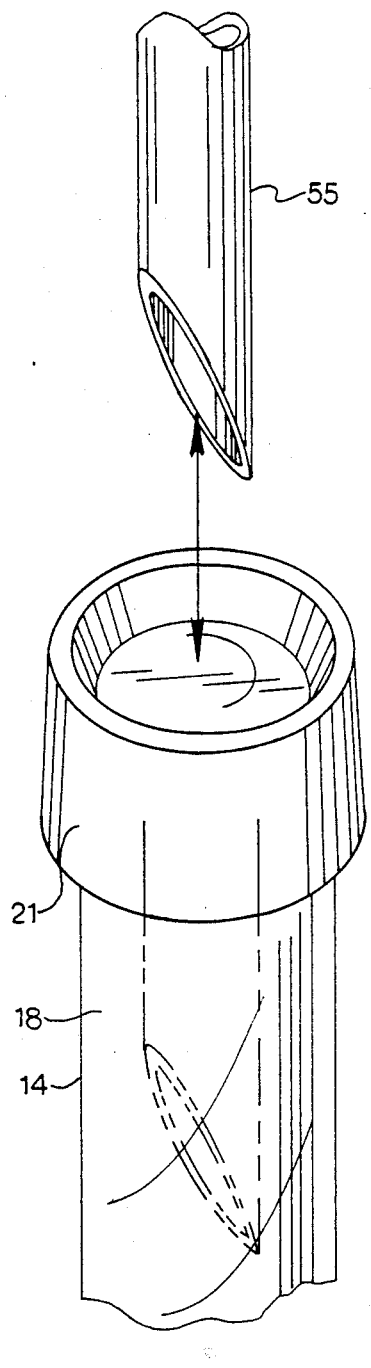
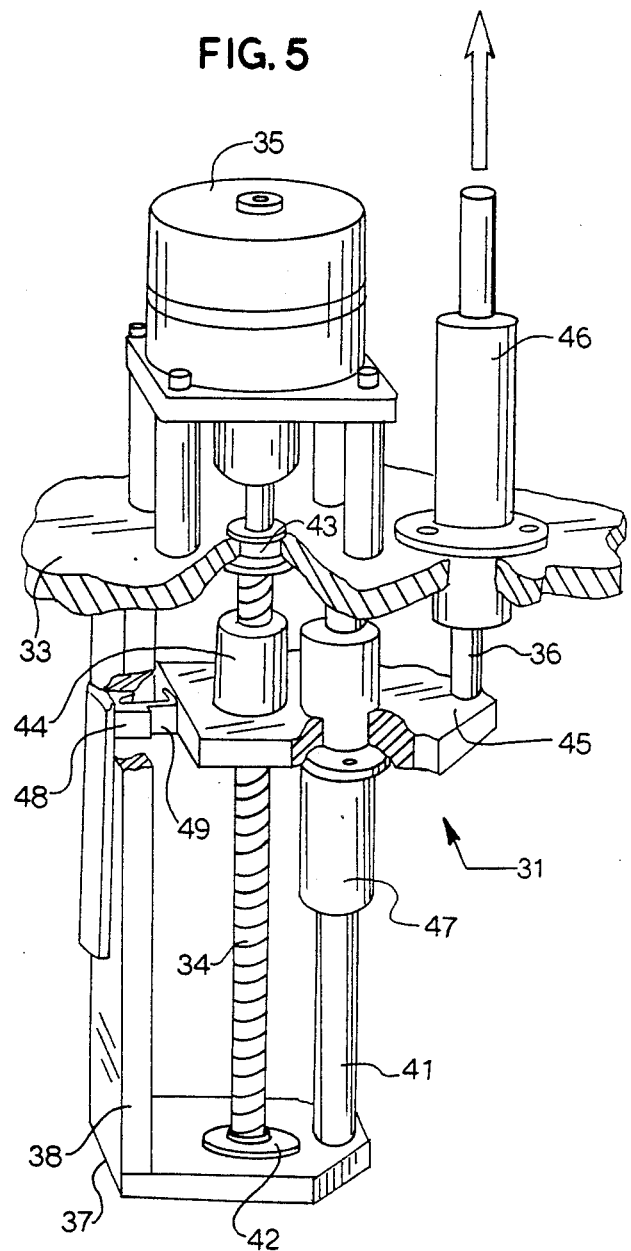

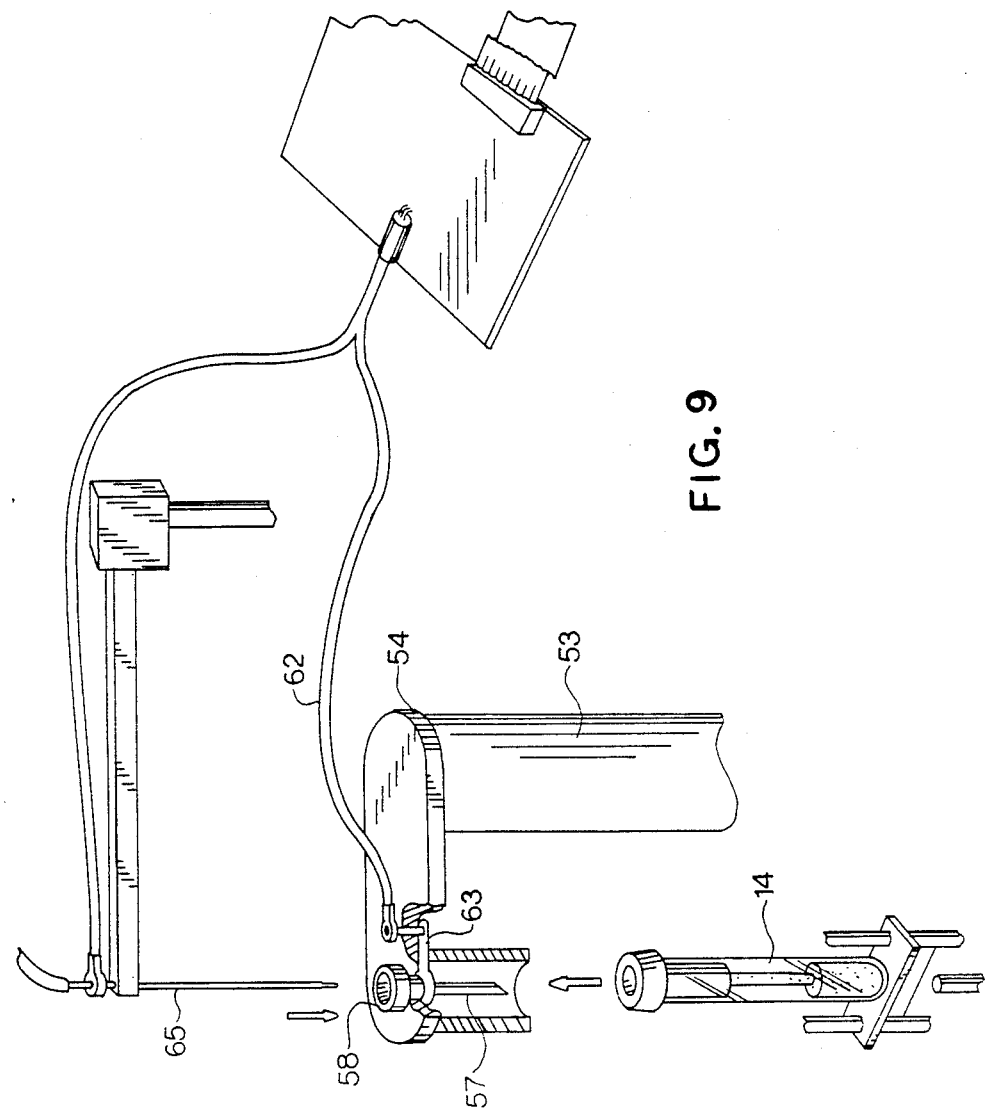
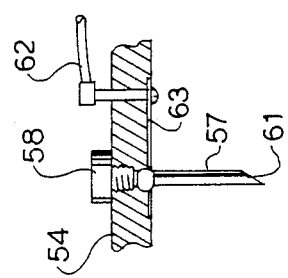

SYSTEM FOR PROVIDING ACCESS TO SEALED CONTAINERS

BACKGROUND OF THE INVENTION

1. Field Of The Invention

The present invention generally relates to a system for providing temporary access to a closed container, and more particularly to an automatic sampler system which provides a temporary opening in the resealable closure of a sample container.

2. Description Of The Prior Art

The prior art provides a number of automatic sampling systems. Generally, these systems receive sample containers, remove a predetermined quantity of sample from each container at a first location, and transfer the removed sample to a second location for analysis. The sample containers usually used with these systems are open-top vials or tubes transported in the system on carousels and transferred between carousels with mechanical push arms or other similar devices.

Samples to be tested in automated sampling systems are most often collected in evacuated containers. These containers generally comprise glass tubes closed with rubber stoppers and sealed with a vacuum. The sample displaces part of the vacuum; but some vacuum may remain. Removal of the stopper may result in the formation of aerosol particles. Consequently, when an operator removes the stopper before placing the container in the automated system, the aerosol spray may expose the operator to any harmful substances contained in the sample. In addition, removal of the stopper manually by the operator increases the cost of operation and decreases the efficiency and reliability of an automated system.

Using open sample containers in an automatic sampling system presents a number of problems. First, the various forces which move the containers through the system cause spills and contamination. Second, open sample containers expose an operator to any harmful substances disposed in the containers. Finally, because open containers require special care, the cost of operation increases.

One solution to these problems is to use closed containers in the automated system. However, most prior systems require the use of open containers. One known automated sampling system (disclosed in U.S. Pat. No. 4,478,095 to Bradley et al.) provides sampling through the stopper of a closed vial. However, to do so, this system includes a complex arrangement of needles, purge mechanisms, and other assemblies. It uses gas pressurization and other complex techniques to take samples from sealed sample containers.

The automated sampling system of the present invention avoids the problems outlined above. The system provides a temporary opening in the closure of a closed sample container in a quick and efficient manner. It allows the system to perform many testing operations through the temporary opening without having to close and reopen the closure. It is a simple, fully automated system which minimizes the expense of manufacture and assembly and gives precise, uniform and reliable performance. This system produces the requisite mechanical action to temporarily open the closure of a sample container and quickly and efficiently establish access to the inside of the container.

SUMMARY OF THE INVENTION

In accordance with one embodiment of this invention, an improved sampling system includes a carousel assembly having a loading carousel which provides sample containers to the system; a transfer carousel for receiving the sample containers from the loading carousel and moving them to a first location where the system takes a sample from them; and an unloading carousel which receives the containers from the transfer carousel and stores them for retrieval by an operator.

Preferably, the system uses glass tube containers, each having an open top and a stopper or cap for closing the opening. Alternatively, the system may use containers of any suitable shape made of any suitable fluid-tight material. The stopper is a self-sealing material such as rubber which can hermetically close a small slit or hole made in it by a slender puncture tube or needle. Other closures, described below, may provide the same closing function.

At the first location, a lift assembly and a puncturing assembly temporarily open the closure of a container placed there by the transfer carousel. The lift assembly coacts with the transfer carousel at the first location to lift the sample container. It lifts the container until the puncturing assembly receives it and forms an opening in its closure using the force provided by the lift assembly.

The transfer carousel has open slots or compartments formed around its periphery and disposed vertically for receiving the sample containers. Each compartment contains a horizontally disposed platform member for supporting a sample container and at least one vertical post fixedly secured at its distal ends to the top and bottom walls of the compartment. This post extends through an opening in the platform member in sliding engagement with the platform member. It secures the platform member in the compartment and allows the platform member to move vertically but not horizontally.

The lift assembly raises and lowers the platform member of the compartment disposed at the first location. This assembly includes a plunger and a conventional lead screw type drive powered by a motor. The lead screw type drive moves the plunger up from a lowered position through an opening in the bottom wall of the transfer carousel compartment at the first location and into engagement with the bottom of the platform member disposed in the compartment. The lead screw type drive continues to move the plunger upward along with the platform member and the container which the platform member supports until a puncture tube of the puncturing assembly engages the closure of the vial and moves completely through the closure to form an opening in it. The system takes a sample or tests the sample through the opening of the puncture tube. After this has occurred, the lead screw type drive lowers the plunger; and the system again closes the vial as described below.

The puncturing assembly includes a support for securing the puncture tube in place above the transfer carousel compartment at the first location This support has the configuration of an inverted "L". The puncture tube is a non-coring, hollow needle with a beveled end having sharp edges and a dull heel. This puncture tube is made out of metal or any other suitable material and it can be electrically connected to the probe or can include an inner plastic sheath which minimizes false triggering of capcitance-sensing liquid detection probes.

Alternatively, the puncture tube may be a hollow member of any suitable shape or any other device which can temporarily penetrate the closure of the sample container to provide an opening through it. Moreover, the closure may be any suitable device with components which allow a penetrating member to displace them and define an opening through the closure.

After the puncture tube establishes communication with the inside of the sample container, a boom assembly moves a probe into the container through the puncture tube. This probe is a tube connected to a pump and reservoir; and it removes a predetermined amount of the sample from the container. The boom and probe assembly then transfers the sample to the cuvettes of a continuous cuvette belt located at a second location. Alternatively, the probe may be a sensor which takes a reading from the sample disposed in the container.

After sampling or sensing, a stripper assembly strips the container from the puncture tube as the lift assembly lowers its plunger and allows the vial to move downward. To perform this function, the stripper assembly includes a push arm and a lead screw type drive powered by a motor. The lead screw type drive moves the push arm from a raised position, into engagement with the top of the container. It continues to move downward until the container's stopper and the puncture tube disengage. After moving the push arm to a predetermined lower position, the lead screw type drive moves the push arm to its raised position.

After the stripper assembly disengages the container from the puncture tube and places it back into the transfer carousel compartment, the drive of the transfer carousel rotates the carousel and brings another compartment to the first location. The sampling continues; and the system transfers the spent vials from the transfer carousel to the storage carousel.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of the preferred embodiment of the sampling system of the present invention.

FIG. 2 is a sectional view of a sample container used in the sampling system of FIG. 1.

FIG. 5 is a side elevation view of the lift assembly of the sampling system of FIG. 1.

FIG. 6 is a side elevation view of the puncture tube and a sample vial, showing the relative displacement of the vial with respect to the puncture tube. The puncture tube appears above the vial in solid lines and inside of the vial in phantom lines after puncturing through the stopper.

FIG. 8 is a sectional view of a puncture tube used in the sampling system of FIG. 1.

FIG. 9 is a sectional view of the puncture tube of FIG. 8 coupled electronically with a liquid level detection probe for use in the sampling system of FIG. 1.

While the applicants will describe the invention in connection with a preferred embodiment, one should understand that the invention is not limited to this embodiment. Furthermore, one should understand that the drawings are not to scale and that the embodiments are illustrated by graphic symbols, diagrammatic representations and fragmentary views. In certain instances, the applicants may have omitted details which are not necessary for an understanding of the present invention such as conventional details of fabrication and assembly.

DETAILED DESCRIPTION OF THE DRAWINGS AND A PREFERRED EMBODIMENT

Figure 3:
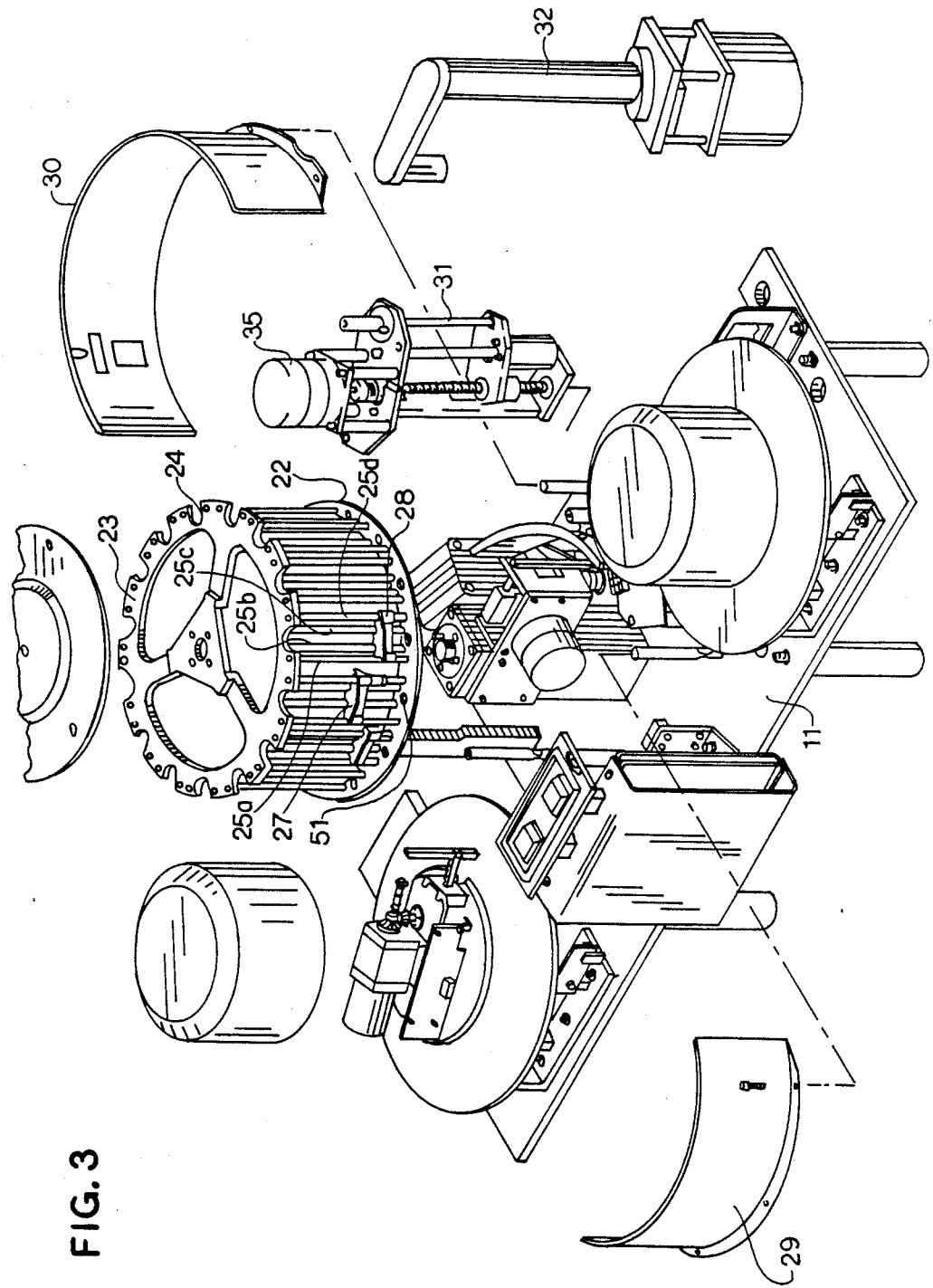
FIG. 3 is a partial exploded view of the system shown in FIG. 1.

Turning now to the drawings, FIGS. 1 and 3 show the preferred embodiment of an improved sampling system according to the present invention generally at 10. This system includes a base plate 11 and a carousel assembly 12 disposed on the base plate. The carousel assembly 12 includes a loading carousel 13 which provides closed sample containers 14 (See FIG. 2) to the system; a transfer carousel 15 for receiving the sample containers 14 from the loading carousel 13 and moving them to a first location 16 where the system opens the sample containers to take a sample or test the sample with a probe; and an unloading carousel 17 which receives the containers from the transfer carousel 15 and stores them for retrieval by an operator. Liston et al. U.S. Pat. No. 4,595,562 entitled "Loading and Transfer Assembly for Chemical Analyzer" generally discloses the carousel assembly 12 in greater detail. With this reference the applicants incorporate the disclosure of that patent to the disclosure of the present application.

The closed container 14 used with the system 10 and shown in FIG. 2 is preferably a glass tube 18 with an open top and a stopper 21 which normally closes the top opening. In addition, the stopper 21 is a self-sealing material, e.g., rubber, which can hermetically close a small slit or hole made in it by a slender puncture tube or needle. Alternatively, the system 10 may use containers of any suitable shape made of any suitable fluid-tight material. Also, the closure may be any suitable device with components which allow a penetrating member to displace them and define an opening through the closure, as described below.

The transfer carousel 15 includes a bottom plate 22 with a flat, ring-like configuration. It also includes a top plate 23 which has the shape of a spoked wheel with semi-circular slots 24 formed in its periphery. The spacing between these slots is constant, and their size and shape generally coincides with the cross-sectional dimensions of the sample container used with the system 10. A set of four posts 25a–d disposed vertically around each slot and secured at one end to the bottom plate 22 and at the opposite end to the top plate 23 define a compartment 26 for receiving a container 14.

Each compartment 26 contains a platform member 27 which supports, raises, and lowers a sample container 14. This platform 27 is a flat, horizontal member with an opening through which the post 25d extends, in sliding engagement with the platform. In addition, the platform 27 has one guide slot and two cutouts formed around its periphery. The guide slot and cutouts receive posts 25a-c and coact with these posts to maintain the platform 27 in alignment in the compartment 26. Finally, the platform 27 includes a guide sleeve 28 secured to the bottom of the platform member 27 and disposed around the post 25d, in sliding engagement with the post 25d, to further maintain the platform horizontally.

Two cover plates 29 and 30 close the compartments 26 around the periphery of the transfer carousel 15, except at the location where the transfer carousel 15 receives a container from the loading carousel 13 and where it transfers the containers to the unloading carousel 17. Suitable connecting devices secure these plates, 29 and 30, to the base plate 11 around the transfer carousel 15. These plates do not contact the transfer carousel 15; they merely prevent the containers 14 from falling out of their compartments 26.

A lift assembly 31 and a puncturing assembly 32, disposed at the first location, temporarily open the closure or stopper 21 of a container 14 placed there by the transfer carousel. The lift assembly drives the platform 27 of the compartment 26 disposed at the first location and raises the container 14 from a lowered position to a raised position. As the lifting assembly 31 lifts the container 14, the puncturing assembly 32 receives it and forms an opening in the stopper 18 using the force provided by the lifting assembly, as described below.

The lift assembly (shown in FIG. 5) includes a horizontal plate 33 for fixedly securing the assembly 31 to the base plate 11. It also includes a lead screw type drive 34 powered by a motor 35 and used to move a plunger 36 vertically between a lowered and raised position. A support frame 37, including an L-shaped member 38 and a guide post 41, maintain the lead screw type drive 34 in vertical alignment, journaled between a bearing 42 secured to the bottom of the member 38 and a bearing 43 secured in an opening through the plate 33. A nut 44 mounted on the lead screw type drive 34 moves vertically in response to the rotation of the lead screw type drive; and a horizontally disposed connecting plate 45 secured to the nut 44 moves with it to drive the plunger 36. To maintain the plunger 36 in vertical alignment, the assembly 31 includes a guide sleeve 46, disposed vertically around the plunger 36 and fixedly secured to the horizontal plate 33. A second guide sleeve 47 disposed vertically around the post 41 and secured to the plate 45 maintains the plate 45 in horizontal alignment.

To control the movement of the nut 44 and, accordingly, the plunger 36, the system 10 includes electronic controls, including a top sensor 48 and a bottom sensor (not shown), which sense the presence of a contact 49 secured to the plate 45. Using the signal provided by these sensors, the electronic controls operate the motor 35 to move the nut 44 between upper and lower limits. The plunger 36 moves from a lowered position where it lies below the bottom plate 22 of the transfer carousel 15 to a raised position. In doing so, it moves through an opening 51 formed in the plate 22 in each compartment 26, engages the bottom of the platform 27, and drives the platform upward and the container 14 which lies on it partially out of the compartment 26 and into engagement with the puncturing assembly 32, as described below.

Figure 4:
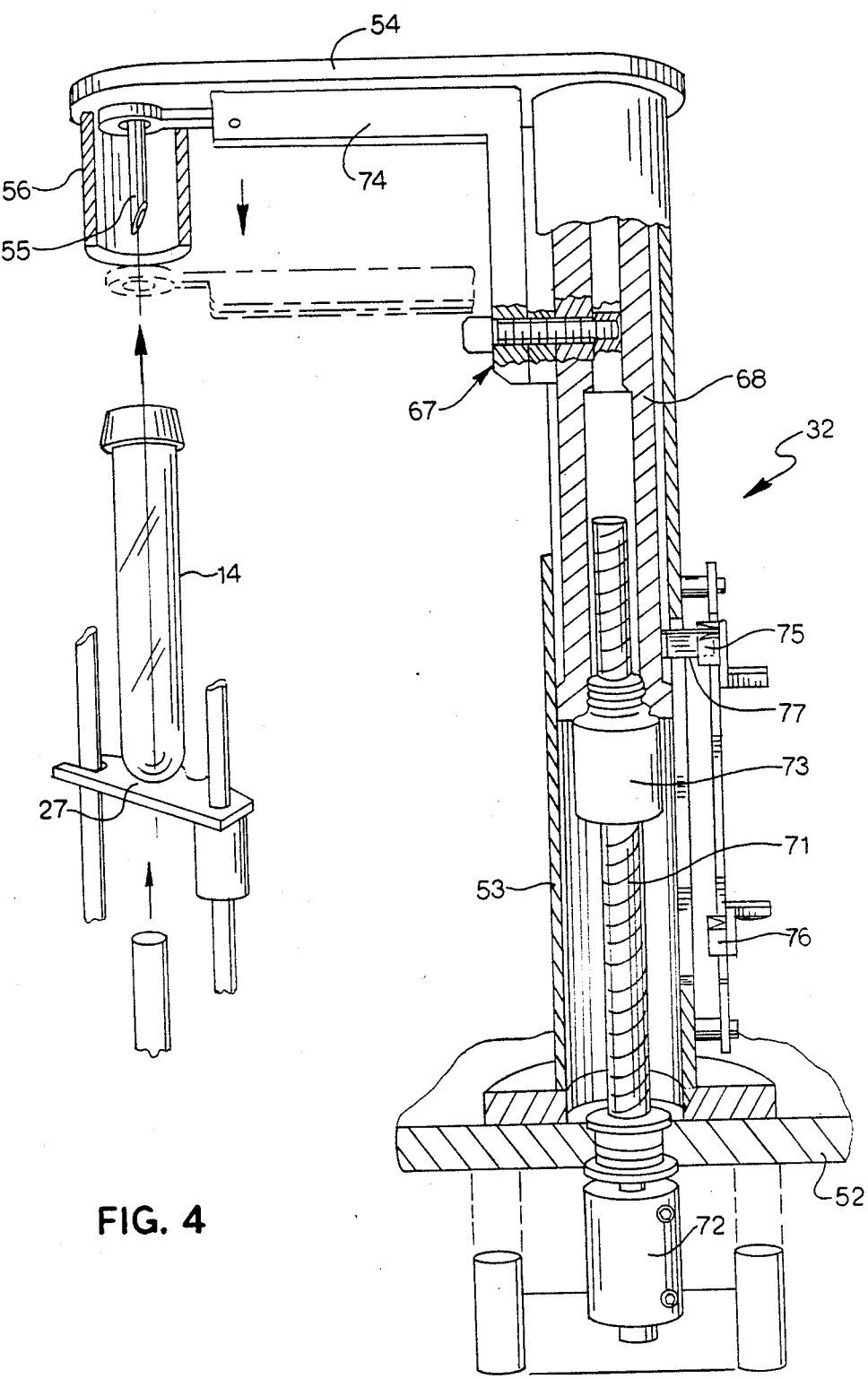
FIG. 4 is a side elevation view of the puncturing assembly and the stripper assembly with portions broken away to expose their construction. This figure also includes a sample container disposed below the puncture tube of the puncturing assembly in axial alignment with the tube.
Figure 7E:
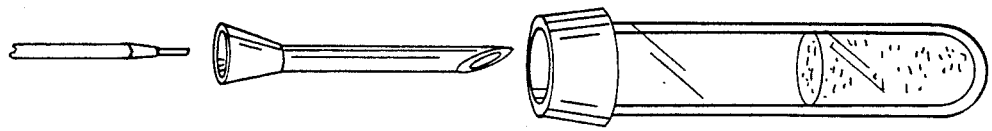
FIGS. 7a–7e are side elevation views of a sample vial used with the sampling system of FIG. 1, showing the sequence of steps included in providing a temporary opening in the stopper of the vial and communicating with the inside of the vial through the opening.
Figure 7D:
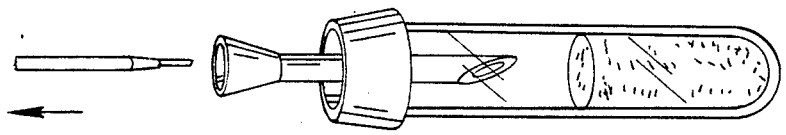
Figure 7C:
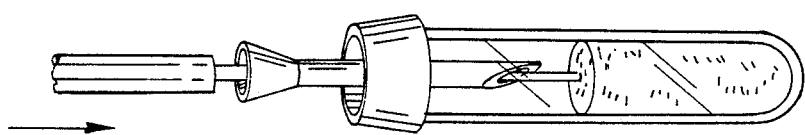
Figure 7B:
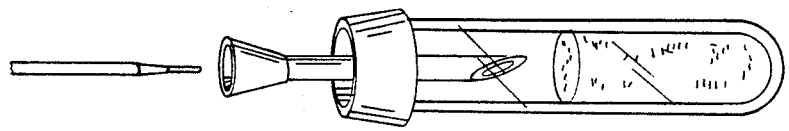
Figure 7A:
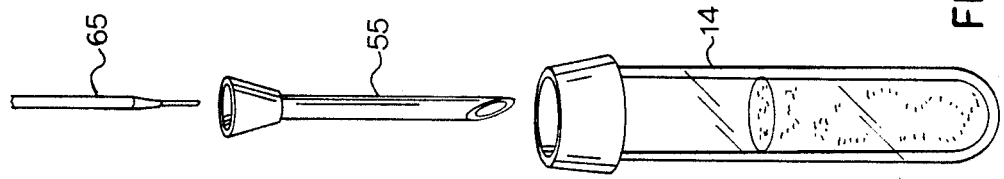

Turning now to FIG. 4, the puncturing assembly 32 includes a securing plate 52 for attaching the assembly 32 to the base plate 11 and a vertical support member 53 fixedly secured to the securing plate 52. The vertical member is a hollow tube made of metal or any other material of high strength and rigidity. It supports a horizontal, cantilever member 54 fixedly secured to its top end. This horizontal support 54 supports a puncture tube 55 (see FIG. 8) in place at the first location 16.

The puncturing assembly also includes a transparent plastic shield 56 with a C-shaped cross-section It lies around the puncture tube 35 secured to the bottom of the horizontal support 54. It receives and centers the top of the container 14 and prevents the operator from touching the sharp end of the needle protecting the operator from injury.

The puncture tube 55 forms an opening in the stopper 21 as shown in FIG. 6 when the lift assembly 31 forces the stopper against the puncture tube. As shown in FIG. 8, it includes a non-coring, hollow needle 57 disposed vertically and downwardly from the support member 54. The top end of the needle 57 lies secured by a press fit or other means in the central opening of a hollow screw 58 which releasably secures it to the horizontal support 54. This hollow screw 55 has a stem portion which fits into a threaded opening formed through the horizontal support 54 and a head which engages the top of the horizontal support. To facilitate the penetration and opening of the stopper 21, the needle 57 has a bevelled bottom end with sharp edges and a dull heel. The screw 58 and needle 57 define a central puncture tube opening 61 through which the system takes a sample or a reading of the sample. To provide a method for detecting liquid upon penetration by the puncture tube 55 and also for minimizing false triggering of capacitance-sensing liquid detecting probes, the puncture tube and the probe can be coupled electronically. The needle 57 is composed of metal and is connected to coaxial cable 62 by a metal spring 63. If upon entering the sample tube, the needle 57 contacts liquid, a change in capacitance will create a signal which will trigger the motor lifting the platform 27 to stop. The coaxial cable is also connected with the metal liquid level detecting sample probe 65 which prevents false triggering of the probe. In an alternative embodiment, a plastic sheath can be used to cover the walls of this opening to minimize false triggering of capacitance-sensing liquid detection probes.

Alternatively, the puncture tube may be a hollow member of any suitable shape or any other device which can penetrate the closure 21 to temporarily provide an opening through the closure. Moreover, the closure may be any suitable device with components which allow a penetrating member to displace them and define an opening through the closure.

After the puncture tube 55 establishes communication with the inside of the container 14, a boom assembly 64 (see FIG. 1) moves the probe 65 into the container through the puncture tube opening 61 (see FIGS. 7a-7e). This probe is a tube connected to a pump and reservoir (not shown); and it removes a predetermined amount of the sample from a container 14. The boom assembly then transfers the sample to the cuvettes 60 of a continuous cuvette belt 66 located at a second location. Alternatively, the probe may be a sensor which takes a reading from the sample disposed in the container 14 or a dispenser for dispensing material into the container.

After sampling, sensing, or dispensing, a stripper assembly 67 (see FIG. 4) disposed in the vertical support 53 of the puncturing assembly 32 strips the stopper 21 from the puncture tube 55 as the lift assembly lowers its plunger 36 and allows the container to move downward. To perform this function, the stripper assembly 67 includes a tubular member 68 disposed in sliding engagement in the hollow support or housing 53. A lead screw type drive 71 powered by a motor 72 drives the member 68 up and down using a nut 73 mounted for vertical movement on the lead screw type drive 71 and secured to the bottom end of the member 68. Secured at the top end of the member 68, a push arm 74 extends through a vertical slot in the housing 53 and engages the stopper 21 at its distal end. This distal end has a flat, configuration with a central opening through which the puncture tube 55 extends. This end segment, ring-shaped, u-shaped or other suitable configuration applies constant downward pressure around the top of the stopper 21, avoiding eccentric loading and tilting of the container 14.

To define the upper and lower limits of movement of the sliding member 63, the electronic controls of the system 10 include a top stripper assembly sensor 75 and a bottom stripper assembly sensor 76 secured to the outside of the housing 53. These devices sense the presence of an optical flag 77. Suitable securing devices secure the optical flag 77 to the member 68; and the flag 77 extends through a vertical slot in the housing 53 to the outside of the housing 53 where the sensors 75 and 76 can detect it. Using the signals provided by these sensors, the system's electronic controls operate the motor 72 to move the nut 73, and thus the push arm 74 between predetermined upper and lower limits. The stripper assembly moves its push arm 74 from a raised position proximate the horizontal support member 54 of the puncturing assembly 32 to a lower position below the bottom end of the puncture tube 55 and back up again.

After the stripper assembly 67 disengages the container from the puncture tube 55 and, along with the lift assembly, lowers the container in the compartment 26, the drive (not shown) of the transfer carousel 15 rotates the carousel and brings the next compartment 26 to the first location 16. The sampling or sensing continues; and the system 10 transfers the spent containers 14 from the transfer carousel 15 to the unloading carousel 17.

While the above description and the drawings illustrate one preferred embodiment, one should understand, of course, that the invention is not limited to this embodiment. Those skilled in the art to which the invention pertains may make modifications and other embodiments employing the principals of this invention particularly, upon considering the foregoing teachings. For example, one skilled in the art may use a drive mechanism to lower the puncture tube rather than use a lift to raise the containers. The applicants, therefore, by the appended claims, intend to cover any modifications and other embodiments as incorporate those features which constitute the essential features of this invention.

What is claimed is:

1. An automated system for providing access to a sealed container and performing sampling operations, said container including closure means, said system comprising:

movable container transfer means for holding the container and moving the container to a first location;

penetrating means disposed at the first location for penetrating the closure means of the container and temporarily defining an opening through the closure;

driving means disposed at the first location for providing relative displacement between the container and the penetrating means at said first location, said driving means providing the force for moving the penetrating means into the container;

probe means separate from the penetrating means for removing sample from the container, placing sample into the container, or sensing the properties of sample in the container, said probe means being movable between the first location and a second location disposed laterally outwardly of the container a predetermined distance from the first location, said probe means also being movable inwardly and outwardly of the opening at the first location to extend in and out of said container through the opening; and stripping means separate from the penetrating means and the probe means for disengaging the penetrating means from the container.

2. An automated system as in claim 1, wherein the penetrating means is stationary and the drive means includes a lift means for moving the container against the penetrating means.

3. An automated system as in claim 1, wherein the penetrating means includes a non-coring, hollow needle and the closure means is a rubber stopper.

4. An automated system as in claim 1, wherein the container transfer means includes a rotatable carousel.

5. An automated system as in claim 1, wherein the stripping means includes a member for engaging the container, said member being moveable relative to the penetrating means and relative to the container transfer means.

6. An automated system as in claim 1 further comprising container means disposed at the second location for receiving material from the probe means or for providing material for the probe means.

7. An automated system as in claim 6, wherein the container means includes a cuvette disposed on a continuous cuvette belt.

8. An automated system as in claim 1, further comprising a shield member disposed proximate the penetrating means.

9. A method of sampling through a closure of a closed container, said method utilizing container transfer means for holding the container and moving the container to a first location, penetrating means disposed at the first location for penetrating the closure of the container and temporarily opening the closure, driving means for providing relative displacement between the container and the penetrating means and for providing the force for moving the penetrating means into the container, probe means separate from the penetrating means for removing sample from the container, placing sample into the container, or sensing the properties of sample in the container, said probe means being movable between the first location and a second location disposed laterally outwardly of the container a predetermined distance from the first location, said probe means also being movable inwardly and outwardly of the opening at the first location to extend in and out of the container through the opening, and stripping means separate from the penetrating means and the probe means for disengaging the penetrating means from the container, said method comprising: forming an opening in the closure of the container with the penetrating means; inserting the probe means through the opening into the container; moving the probe means out of the container and to the second location; and disengaging the penetrating means from the container to allow the opening in the closure to close.

* * * * *